United States Patent [19]
Eyal

[11] Patent Number: 5,831,122
[45] Date of Patent: Nov. 3, 1998

[54] PROCESS AND EXTRACTANT COMPOSITION FOR EXTRACTING ACIDS

[75] Inventor: Aharon Meir Eyal, North Judaea, Israel

[73] Assignee: Yissum Research Development Company of the Hebrew University of Jerusalem, Jerusalem, Israel

[21] Appl. No.: 716,154

[22] PCT Filed: Mar. 13, 1995

[86] PCT No.: PCT/GB95/00535

§ 371 Date: Nov. 12, 1996

§ 102(e) Date: Nov. 12, 1996

[87] PCT Pub. No.: WO95/25081

PCT Pub. Date: Sep. 21, 1995

[30] Foreign Application Priority Data

Mar. 16, 1994 [IL] Israel ........................................ 109003

[51] Int. Cl.$^6$ .................................................. C07C 51/42
[52] U.S. Cl. ............................................................ 562/580
[58] Field of Search .............................................. 562/580

[56] References Cited

U.S. PATENT DOCUMENTS 4,275,234  6/1981  Baniel et al. ............................ 562/580

*Primary Examiner*—Paul J. Killos
*Attorney, Agent, or Firm*—Sughrue, Mion, Zinn, Macpeak & Seas, PLLC

[57] ABSTRACT

The invention provides a process for the recovery of a water-soluble carboxylic or mineral acid having a pKa higher than 2 from an aqueous feed solution containing the acid or a salt thereof, comprising extracting the acid with a water-immiscible extractant composition, the composition comprising: (a) at least one secondary or tertiary aklyl amine, in which the aggregate number of carbon atoms is at least 20, as a primary extractant; and (b) a sterically hindered, polar, organic compound having at least 5 carbon atoms, a basicity weaker than that of the primary extractant, and temperature-sensitive, extraction-modifying properties; separating the acid containing the extractant and subjecting it to a stripping operation at a temperature of at least 20° C. higher than the temperature at which the extraction is carried out, wherein the sterically hindered, polar, organic compound both modifies the extracting power of the primary extractant composition and facilitates the temperature-sensitive stripping operation. The invention also provides an extractant composition for use in such a process.

20 Claims, No Drawings

PROCESS AND EXTRACTANT COMPOSITION FOR EXTRACTING ACIDS

The present invention relates to a process and extractant composition for extracting and recovering acids from aqueous solutions.

More particularly, the present invention relates to an improved extractant composition and process for the recovery of a water-soluble carboxylic or mineral acid having a pKa higher than 2, from an aqueous solution containing said acid or salt thereof.

Acid-containing aqueous streams are obtained in many industrial processes such as chemical and biosynthesis of acids, leaching, surface treatment, etc. Of particular interest to the present invention are fermentation liquors comprising carboxylic acids of relatively low concentrations or fermentation liquors comprising salts of carboxylic acids. Two important examples are the fermentation liquor comprising about 15% citric acid and the one comprising a lactate salt. (Lactic acid fermentation is usually maintained at pH of about 5 or higher by addition of a base. The fermentation liquors thus contain mainly the lactate salt). The recovery of the acids from such liquors accounts for a major part of total production cost.

Traditional separation methods are based on consuming reagents, and thus also entail the production of by-products requiring disposal. These are avoided on using liquid-liquid extraction, which has additional important advantages, such as low energy consumption and avoidance of high temperatures that may lead to unwanted reactions of the product. In liquid-liquid extraction, the aqueous solution (feed) is contacted with an extractant, preferably in a multi-stage, counter-current operation. Some components transfer from the aqueous phase to the extractant. The loaded extractant (extract) is separated and treated in a separate operation to recover the extracted components and to regenerate the extractant. Many basic organic compounds were found suitable for extraction of acids, including alkanols, aldehydes, ketones, ethers, esters, amines, trialkyl phosphates and phosphine oxides.

Long straight chain amines are in many cases most desired extractants due to high efficiency, high selectivity and low miscibility in the aqueous phase. Amines are usually used in a diluent to avoid high viscosity, particularly in the acid-loaded extract. The diluent, or a third component, may also provide for modification of extractant properties. Thus, Baniel, et al. (U.S. Pat. Nos. 4,291,007 and 4,334,095) have found that adding an organic acid to the extractant provides for easier back-extraction of the extracted acids, while having just a limited suppressing effect on forward extraction.

It is well known that polar and protic compounds provide for enhancement of acid extraction by amines (Wojtech, et. al., U.S. Pat. No. 4,720,577). These compounds may act as acid extractants by themselves, but are much weaker extractants than the amines. Extractants comprising amines and enhancers show, in most cases, synergistic effects, i.e., acid extraction by such extractants is much higher than the added contribution of the components.

In the description hereinafter, and to avoid confusion, the term "primary extractant" will be used for relatively strong, long chain amines used for extractions, and the term "enhancer" for polar extractant components, the extraction power of which is smaller than that of the primary extractant. Relatively weak amines are considered enhancers when present in extractants comprising relatively strong amines as the primary extractant.

Desired extractants should provide for high efficiency in extraction (relatively low extractant volumes and small number of extraction stages), high selectivity, low water miscibility, low toxicity (particularly for food grade products) and for efficient stripping of the extracted acid from the extract. The latter can be removed from the extract through interaction with an aqueous solution of a base. In most cases, however, the acid is the required product rather than the salt, and acid recovery from the extract is performed by back-extraction with water, or by distillation.

As is known, high efficiency in extraction from the feed and high efficiency in back-extraction are conflicting requirements. Back-extraction of the extracted acid from a strong extractant requires high volumes of water and results in a very dilute aqueous solution of the acid (back-extract). The high cost of product concentration may make the whole process impractical. Distillation from a strong extractant requires high temperatures.

An important discovery was made by Baniel, et al. (U.S. Pat. No. 4,275,234). On extraction of carboxylic and weak mineral acids, amine-based extractants lose some of their extraction efficiency on temperature elevation.

This phenomenon, referred to as "temperature sensitivity of the extracting power of the extractant composition" or just "temperature sensitivity," enables effective extraction at lower temperatures, while allowing for effective stripping or back-extraction at higher temperatures, due to the decrease of the extraction efficiency of the primary extractant at higher temperatures.

As explained in U.S. Pat. No. 4,275,234:

The concepts of "lower temperature" and "higher temperature" are not understood in absolute terms. What matters . . . is the temperature differential. This will have to be at least 20 degrees (centigrade), both for operation convenience and in order to make both the extraction and the back-extraction as complete as possible. The extraction may be carried out at temperatures as low as near the freezing point of the aqueous acid solution and the temperature of the back-extraction may be at or near the boiling point of the extract or the water at atmospheric pressure, or if the back-extraction is carried out under elevated pressure, at an even higher temperature, always on condition that the temperature and pressure are so chosen that the amine remains in the organic phase. In many cases the extraction can be carried out at or near room temperature, and the stripping operation at a temperature of about 20 to 40 degrees (Centigrade) above room temperature. As a rule, the stripping operation is the more effective, the higher the stripping temperature, but the extraction and stripping temperatures will be selected in individual cases in accordance with practical factors, such as corrosion-resistance and the costs of the equipment, costs of heating and cooling of the streams of the acid solution, the extract and the extractant, the required concentration of stripped acid, etc.

If the aqueous liquid used for stripping the extract is water, the back-extract is an aqueous solution of the free acid. If desired, the back-extracting operation may be so conducted that the back-extract is an aqueous solution of a salt of the extracted acid. For example, back-extraction with an aqueous alkali metal (in this context "alkali metal" includes ammonium) hydroxide solution yields an aqueous solution of the corresponding alkali metal salt of the extracted acid. Or the aqueous back-extracting liquid may be, for example, an alkali metal chloride solution. In this case, too, the back-extract contains the corresponding alkali metal salt of the extracted acid while the amine in the extractant is converted into its hydrochloride. This will thus have to be decomposed, e.g. by treatment with calcium hydroxide, for reconstituting the extractant. Sometimes it is advantageous to perform first a back-extraction with water in order to recover the major part of the acid in the free state. The residue of acid remaining in the solvent extract can then be back-extracted with an alkali metal hydroxide or salt solution.

"The most favourable selection of the temperature of the extracting operation and of the compositions of the extractant, as regards both the amine and the solvent, will also be determined according to the given condition of particular cases, e.g., the kind of acid, its concentration in the original aqueous solution, the impurities present in that solution. The major aim in both the extracting and stripping operations will be to achieve as favourable a distribution coefficent as possible for the distribution of the acid between the aqueous and organic phases. In the extraction operation, this has to be in favour of the extractant; in the stripping operation, in favour of the aqueous phase."

In the Baniel, et al., process, back-extraction is performed at a temperature higher than that of the extraction. For certain acids, they have shown efficient extraction at about room temperature. Back-extraction at about 100° C. provides for a back extract, the concentration of which is similar to, or even higher than, that of the feed. A major part of citric acid production in the world is based on this process, using tridodecyl amine as the primary extractant and 1-octanol as the enhancer [Kirk-Othmer, encyclopedia cf Chemical Technology 4th Ed., Vol. 6, p. 364].

Similarly, Marrs et al. (AT-C-379–582) describes a method of extraction, wherein the back-extraction process involves use of a stripping acid.

Extractants comprising relatively strong amines as the primary extractant, show nearly no temperature sensitivity on the efficiency of extracting strong mineral acids. It was, however, found that relatively weak amines do show such effect. An example of such weak amines is the sterically-hindered, branched chain amines with branching on a carbon close to the nitrogen atom [Eyal, et. al., Solvent Extraction and Ion Exchange, Vol. 9, pp. 195–236 (1991)]. These amines are weaker by more than two orders of magnitude than straight chain amines, and weaker than branched chain amines with branching far from the nitrogen atom. Such amines are too weak to extract most weak acids and are not suitable for use as primary extractants in the present invention. For simplicity of language, the term "branched chain amines" will be used here just for sterically hindered, relatively weak amines with branching close to the nitrogen atom.

Branched chain amines are too weak to extract many of the carboxylic acids, particularly hydroxycarboxylic acids. Straight chain amines are much more efficient, but complete extraction without resorting to high cooling costs requires the use of extraction enhancer. This is particularly true for extraction from dilute feed solutions. Yet, the stronger is the enhancer and the higher its contents, the lower is the sensitivity of extraction efficiency to temperature. Thus, amine-based extractants, comprising relatively strong enhancers at high proportions of enhancers, show high efficiency in extraction, but lose most of the advantage in back-extraction at higher temperature, according to U.S. Pat. No. 4,275,234.

According to the known practice, there have been suggested four main options, as well as variations and combinations thereof:

a) Use of a weak enhancer or a strong enhancer, at a minimal concentration required for extraction completion (non-optimal extractant composition in extraction, high extractant volume, many stages in extraction). This option was chosen for the citric acid production.

b) Increase the temperature span between extraction and back-extraction (expensive cooling and high viscosity in extraction, and expensive heating and thermal degradation in back-extraction).

c) Distill at least part of the enhancer from the extract prior to back-extraction (high energy cost, limitation to volatile enhancers that in most cases have relatively high solubility in the aqueous streams, requiring additional recovery operations).

d) Add to the extract an a-polar solvent that acts as extraction suppressor, and removal of this solvent prior to the use of the regenerated extractant (low efficiency, high energy cost).

In contradistinction to the above options, a first aspect of the present invention is based on the discovery that polar organic compounds with steric hinderance of the polar group have, at about ambient temperature, an enhancement effect similar to that of similar non-hindered compounds, but lower enhancement effect at elevated temperature. As a result, efficient extraction is achievable using amine-based extractants at about ambient temperature, in combination with convenient amounts of enhancer, while efficient back-extraction is achieved at elevated temperature, without resorting to unduly high temperatures in back-extraction and/or high energy-consuming removal of extractant components, either prior to back-extraction or after it.

Furthermore, it is well known that enhancer-containing extractants provide for more efficient extraction, but at the cost of reduced temperature sensitivity of the extracting power. The advantage of enhancer application in the extraction may be out-balanced by the reduced temperature sensitivity. Thus, for extraction of an acid from an aqueous feed of a relatively high acidity, particularly if incomplete extraction can be tolerated, non-enhanced (or slightly enhanced) extractants are preferred. On the other hand, in extraction from dilute aqueous solutions of acids, and particularly in extraction from aqueous solutions of relatively high pH, an enhanced extractant is essential for efficient extraction (alternatively, a non-enhanced, very strong amine can be used as a primary extractant, but stripping is impractical for such extractants).

Lactic acid production by fermentation is product-inhibited. The pH in the fermentation liquor should, therefore, be maintained by the addition of a base, at a pH of about 5, and preferably above 6. At this pH, nearly all the lactic acid (pKa=3.86) is converted to its salt form, and acid activity is negligible. No extraction of lactic acid is observed on contacting this solution with a tertiary amine-comprising extractant. In the presence of a weak acid and/or pressurized $CO_2$, some extraction takes place. Yet, it was found that in order to reach suitable extraction at a reasonable $CO_2$ pressure, the extractant should be enhanced by a strong enhancer, i.e., by a polar, and preferably protic, organic enhancing compound. It was surprisingly found that sterically hindered enhancers, which facilitate the temperature-sensitive stripping operation, are strong enough enhancers to augment the extraction of an acid from feed solutions at a pH higher than the pKa.

Thus, the present invention now provides a process for the recovery of a water-soluble carboxylic or mineral acid having a pKa higher than 2, from an aqueous feed solution containing said acid or a salt thereof, comprising extracting said acid with a water-immiscible extractant composition, said composition comprising (a) at least one secondary or tertiary alkyl amine, in which the aggregate number of carbon atoms is at least 20, as a primary extractant; and (b) a sterically hindered, polar, organic compound, having at least 5 carbon atoms, a basicity weaker than that of said primary extractant, and temperature-sensitive, extraction-modifying properties; separating the acid containing said extractant and subjecting it to a stripping operation at a temperature of at least 20° C. higher than the temperature at which said extraction is carried out, wherein said sterically hindered, polar, organic compound both modifies the extracting power of said primary extractant composition and facilitates said temperature-sensitive stripping operation.

In preferred embodiments of the present invention, said sterically hindered, polar, organic compound is selected from the group consisting of alkanols, carboxylic acids, tertiary amines, or trialkylphosphates, having a sterically hindering substituent attached to the carbon carrying said polar group, or to a carbon which is alpha, beta, or gamma to said carbon.

Depending on the desired process and the nature of the acid or salt and the primary extractant, said sterically hindered, polar, organic compound can be an extraction inhibitor, functioning, e.g., as a weak inhibitor at low temperature, and as a stronger inhibitor at higher temperature; or as an extraction enhancer having stronger extraction-enhancing activities at low temperatures than at higher temperatures. Said stripping or back-extraction operation can be effected with an aqueous solution, or even by distillation. In the latter case, the compound used will have a boiling point at about at least 10° above the stripping temperature at the stripping operating pressure.

Polar, and particularly protic, organic compounds act as enhancers of acid extraction by amines, due to their ability to solvate the amine acid ion pair formed on such extraction. Organic compounds suitable for use as enhancers in the present invention have at least one such polar or protic group, the solvating properties of which are hindered by the structure of the molecule. The polar group is preferably a hydroxyl, an ester, an aldehyde, a carboxyl, a ketone, or an amine, or said polar group can comprise a halogen, sulfur, nitrogen or phosphate atom. The hindrance can be achieved through substitution of a hydrogen atom in the alkyl chain by an aliphatic group, i.e., branching on the carbon atom carrying the polar group, or on a carbon which is alpha, beta, or gamma to said carbon.

The enhancer should be a weaker base than the amine used as the primary extractant in the extractant composite. On equilibrating it with a 0.1M aqueous HCl solution in a proportion that provides for enhancer to HCl molar ratio of 2, the aqueous phase pH will remain below 2. On a similar equilibration, with the amine acting by itself as the non-enhanced extractant, the pH of the aqueous phase increases to about 2.5 or higher.

The extractant comprises at least one secondary or tertiary alkylamine, the aggregate number of carbon atoms of which is at least 20, as the primary extractant. Particularly suitable amines are the commercially available trioctyl, tricaprylyl, tridecyl, and tridodecyl amines.

In addition to the primary extractant and the sterically-hindered, polar, organic enhancer compound, the extractant may comprise a water-immiscible, polar or non-polar solvent, for example, aliphatic or aromatic hydrocarbon, hydrocarbons carrying nitro or halo substituents, and alcohols.

In preferred embodiments of the present invention, said sterically hindered, polar, extraction-enhancing compound is selected from the group consisting of secondary or tertiary alkanols, tris-2-ethylhexyl amine, and tris-2-ethylhexyl phosphate.

As indicated, the present improved process is especially applicable to recovering hydroxycarboxylic acids such as citric acid and lactic acid, and can be used to modify and replace the commercially-used process for the preparation of citrus acid, e.g., by replacing 1-octanol in the extractant composition with a sterically hindered, polar, organic compound having at least 5 carbon atoms and a basicity weaker than that of said primary extractant, as taught by the present invention.

In another preferred embodiment of the present invention, the process is carried out with an aqueous feed solution having a pH higher than the pKa of the acid to be extracted. Preferably, the pH should be higher by at least one unit than the pH of said acid.

As is known, when the pH of the feed solution is equal to the pKa of the acid to be extracted, about 50% of the acid is neutralized; while when the pH is one unit higher than the pKa of the acid to be extracted, about 90% of said acid is neutralized.

Therefore, as explained hereinabove, the present invention could be used to recover lactic acid, said extraction being performed in the presence of $CO_2$ and said primary extractant being a tertiary alkyl amine.

The present invention also provides an extractant composition for use in a process for the recovery of a water-soluble, carboxylic or mineral acid having a pKa higher than 2, from an aqueous feed solution containing said acid or a salt thereof, said composition comprising (a) at least one secondary or tertiary alkyl amine, in which the aggregate number of carbon atoms is at least 20, as a primary extractant; and (b) a sterically hindered, polar, organic compound having at least 5 carbon atoms, a basicity weaker than that of said primary extractant, and temperature-sensitive, extraction-modifying properties.

In a preferred embodiment of the present invention, particularly if the pH of the aqueous feed is higher than the pKa of said acid, the extraction can be performed in the presence of another weak acid, or in the presence of $CO_2$.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

The temperature sensitivity of the extracting power of the extractant composition is shown by comparing distribution co-efficients - D (extracted acid concentration in the organic phase in equilibrium, divided by its concentration in the aqueous phase in equilibrium). Temperature sensitivity is reflected in D decrease, with temperature elevation. A higher $D_{RT}/D_T$ ratio indicates higher temperature sensitivity (D at ambient temperature, divided by D at an elevated temperature T).

Table 1 summarizes $D_{RT}/D_{95°C}$ for lactic acid extraction by extractants comprising 50% w/w Alamine 336 (tricaprylyl amine produced by Henkel), 20% W/W enhancer, and 30% of a low aromatics kerosene. Acid concentration in equilibrium aqueous phases, at both temperatures, was 0.5 mol/kg.

TABLE 1

| Enhancer | $D_{RT}/D_{95°C}$ |
|---|---|
| 1-Octanol | 2.3 |
| 3-ethyl-3-pentanol | 4.4 |
| 2,4-dimethyl-3-pentanol | 3.3 |
| 6-undecanol | 4.2 |
| tris-(2-ethylhexyl)amine | 8.5 |
| tris-(2-ethylhexyl) phosphate | 7.5 |

These results indicate that extractant compositions containing sterically hindered, polar, organic enhancers show higher temperature sensitivity than n-octanol-containing extractant compositions. For most of the enhancers in Table 1, enhancement at ambient temperature was similar to that of n-ctanol.

Table 2 summarizes $D_{RT}/D_{95°C}$ for citric acid extraction by extractants comprising 55% Alamine 304 (tridodecyl amine produced by Henkel), 6% enhancer, and 39% low aromatics kerosene. Citric acid concentration in equilibrium aqueous phases, at both temperatures, was 0.5 mol/kg.

TABLE 2

| Enhancer | $D_{RT}/D_{95°C}$ |
|---|---|
| n-Octanol | 2.0 |
| 4-methyl-2-pentanol | 2.4 |
| 3-ethyl-3-pentanol | 4.3 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of a water-soluble carboxylic or mineral acid having a pKa higher than 2, from an aqueous feed solution containing said acid or a salt thereof, comprising:

contacting said aqueous feed solution with a water-immiscible extractant composition, said composition comprising:

(a) at least one secondary or tertiary alkyl amine, in which the aggregate number of carbon atoms is at least 20, as a primary extractant; and (b) a sterically hindered, polar, organic compound having at least 5 carbon atoms, a basicity weaker than that of said primary extractant, and temperature-sensitive, extraction-modifying properties;

extracting said acid from said aqueous feed solution;

separating the extractant containing the acid from the aqueous feed solution; and subjecting the extractant containing the acid to a stripping operation at a temperature of at least 20° C. higher than the temperature at which said extraction is carried out, wherein said sterically hindered, polar, organic compound both modifies the extracting power of said primary extractant composition and facilitates said stripping operation.

2. A process according to claim 1, wherein said sterically hindered, polar, organic compound is an extraction enhancer.

3. A process according to claim 1, wherein said sterically hindered, polar, organic compound is selected from the group consisting of alkanols, carboxylic acids, tertiary amines, and trialkylphosphates having a sterically hindering substituent attached to the carbon carrying said polar group, or to a carbon which is alpha, beta, or gamma to said carbon.

4. A process according to claim 3, wherein said substituent is an aliphatic group.

5. A process according to claim 2, wherein said sterically hindered, polar, organic compound is selected from the group consisting of secondary or tertiary alkanols, tris-2-ethylhexyl amine, and tris-2-ethylhexyl phosphate.

6. A process according to claim 1, wherein the recovered acid is a hydroxycarboxylic acid.

7. A process according to claim 6, wherein the recovered acid is citric acid.

8. A process according to claim 6, wherein the recovered acid is lactic acid.

9. A process according to claim 1, wherein the aqueous solution of said acid or its salt is obtained by fermentation.

10. A process according to claim 1, wherein the extraction is performed in the presence of another weak acid.

11. A process according to claim 1, wherein the extraction is performed in the presence of $CO_2$.

12. A process according to claim 1, wherein the boiling point of said compound is at least 10° C. above the stripping temperature at the stripping operating pressure.

13. A process according to claim 1, wherein said stripping operation is effected with an aqueous liquid.

14. A process according to claim 1, wherein said stripping operation is effected by distillation.

15. A process according to claim 1, wherein said aqueous feed solution is at a pH higher than the pKa of said acid.

16. A process according to claim 1, wherein the pH of said aqueous feed solution is higher by at least one unit than the pKa of said acid.

17. A process according to claim 16, wherein said acid is lactic acid.

18. A process according to claim 17, wherein said extraction is performed in the presence of $CO_2$, and wherein said primary extractant is a tertiary alkyl amine.

19. An extractant composition for use in a process for the recovery of a water-soluble, carboxylic or mineral acid having a pKa higher than 2, from an aqueous solution containing said acid or a salt thereof, said composition comprising:

a) at least one secondary or tertiary alkyl amine in which the aggregate number of carbon atoms is at least 20, as a primary extractant; and
b) a sterically hindered, polar, organic compound having at least 5 carbon atoms, a basicity weaker than that of said primary extractant, and temperature-sensitive, extraction-modifying properties,
wherein said sterically hindered, polar, organic compound is selected from the group consisting of alkanols, carboxylic acids, tertiary amines, or trialkylphosphates having a sterically hindering substituent attached to the carbon carrying said polar group, or to a carbon carrying said polar group, or to a carbon which is alpha, beta, or gamma to said carbon.

20. An extractant composition as claimed in claim 19, further comprising a water-immiscible, organic solvent.

* * * * *